United States Patent [19]

Cartwright

[11] Patent Number: 4,508,907

[45] Date of Patent: Apr. 2, 1985

[54] 2,3-DICHLORO-5-TRICHLOROMETHYL-PYRIDINE

[75] Inventor: David Cartwright, Woodley, England

[73] Assignee: Imperial Chemical Industries, PLC, London, England

[21] Appl. No.: 431,373

[22] Filed: Sep. 30, 1982

Related U.S. Application Data

[63] Continuation of Ser. No. 29,341, filed as PCT GB 78/00008, Aug. 10, 1978, published as WO 79/00094, Mar. 8, 1979, § 102(e) date Apr. 11, 1979.

[30] Foreign Application Priority Data

Aug. 12, 1977 [GB] United Kingdom ............... 34039/77
Oct. 26, 1977 [GB] United Kingdom ............... 44541/77
Feb. 9, 1978 [GB] United Kingdom ................. 5230/78
Aug. 10, 1978 [WO] PCT Int'l Appl. ... PCT/GB78/00008

[51] Int. Cl.³ .......................................... C07D 213/26
[52] U.S. Cl. ........................................ 546/345; 71/94; 546/291; 546/302
[58] Field of Search ........................................ 546/345

[56] References Cited

U.S. PATENT DOCUMENTS

| | | | |
|---|---|---|---|
| 3,244,722 | 4/1966 | Johnston et al. | 546/345 |
| 4,184,041 | 1/1980 | Nishiyama et al. | 546/345 |
| 4,317,913 | 3/1982 | Cartwright | 546/345 |
| 4,324,627 | 4/1982 | Cartwright | 204/158 HA |

FOREIGN PATENT DOCUMENTS 0009212  4/1980  European Pat. Off. ............ 546/345

Primary Examiner—Richard A. Schwartz
Attorney, Agent, or Firm—Cushman, Darby & Cushman

[57] ABSTRACT

Herbicidal pyridine compounds of the formula:

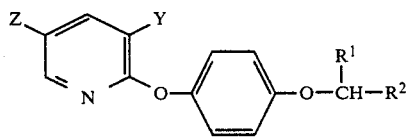

are disclosed, wherein the various substituents are defined hereinbelow. Also disclosed are intermediates used in the preparation of I, including 2,3-dichloro-5-trichloromethylpyridine.

1 Claim, No Drawings

2,3-DICHLORO-5-TRICHLOROMETHYLPYRIDINE

Continuation of Ser. No. 29,341, filed as a PCT GB 78/00008, Aug. 10, 1978, published as WO 79/00094, Mar. 8, 1979, § 102(e) date Apr. 11, 1979.

This invention relates to certain pyridine derivatives having herbicidal properties, and to herbicidal processes and compositions utilising them.

According to the present invention there are provided herbicidal pyridine compounds of the formula (I):

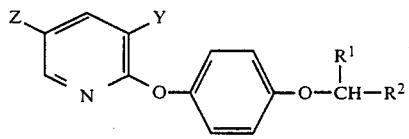

wherein Z and Y each represent a fluorine, chlorine, bromine, iodine, or hydrogen atom, or a trifluoromethyl, difluoromethyl, or chlorodifluoromethyl radical, provided that at least one of Z and Y is a halogenomethyl radical; $R^1$ represents hydrogen or an alkyl radical of 1 to 4 carbon atoms; and $R^2$ is a cyano group; a carboxyl group; a carboxamido group

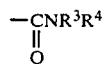

wherein $R^3$ is hydrogen or an alkyl radical and $R^4$ is hydrogen, an optionally hydroxy- or phenyl-substituted alkyl radical of 1 to 4 carbon atoms, a phenyl or chlorophenyl radical, an alkoxy radical of 1 to 4 carbon atoms, or a group —$NR^5R^6$ wherein $R^5$ is hydrogen or alkyl of 1 to 4 carbon atoms, and $R^6$ is hydrogen, alkyl of 1 to 4 carbon atoms, phenyl or chlorophenyl, or the group —$NR^3R^4$ constitutes a pyrrolidino, piperidino, or morpholino radical; a group

wherein $R^7$ is alkyl or phenyl; an alkoxycarbonyl group wherein the alkoxy group may be straight or branched, and which optionally bears one or more hydroxy, alkoxy, or halogen substituents, or bears a substituent of Formula (I) wherein $R^2$ represents a

radical; a group

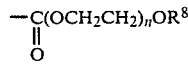

wherein $R^8$ is an alkyl radical of 1 to 4 carbon atoms and n is an integer from 1 to 5 inclusive; a cyclohexyloxycarbonyl radical optionally substituted by one or more halogen atoms or methyl radicals; an alkenyloxycarbonyl radical in which the alkenyl group contains from 3 to 6 carbon atoms; a phenoxycarbonyl radical optionally bearing one or more halogen or methyl substituents; or a benzyloxycarbonyl radical, the phenyl group of which optionally bears one or more halogen or methyl substituents; and, in the case of compounds wherein $R^2$ is a carboxyl group, salts thereof.

When $R^3$ is an alkyl radical it is preferably an alkyl radical of 1 to 12 carbon atoms, for example an alkyl radical of 1 to 4 carbon atoms.

When $R^7$ is an alkyl radical it may be for example an alkyl radical of 1 to 20 carbon atoms. Examples of alkyl radicals within this range include those of 1 to 12 carbon atoms, for example methyl, ethyl, propyl, butyl, and dodecyl.

When $R^2$ is an alkoxycarbonyl group, the alkoxy group may contain for example from 1 to 20 carbon atoms; it may for example contain from 1 to 12 carbon atoms. Within this range, the alkoxy group may for example contain from 1 to 8 carbon atoms. Particular examples of alkoxy groups within this range include methoxy, ethoxy, propoxy, butoxy, isobutoxy, sec-butoxy, and octyloxy.

Salts of compounds according to the invention wherein $R^2$ represents a carboxylic acid may be prepared by conventional methods known for the preparation of salts of carboxylic acids. Typical salts include metal salts and ammonium salts. Metal salts include salts formed with alkali metal cations, for example sodium, potassium and lithium, and alkaline earth metal cations, for example calcium, strontium, and magnesium. Ammonium salts include salts formed with the ammonium cation or with a mono-, di-, tri-, or tetra-substituted ammonium cation in which the substituents may be, for example, aliphatic radicals of 1 to 6 carbon atoms; these may be, for example, alkyl radicals of 1 to 6 carbon atoms.

One group of compounds according to the invention includes those in which the group Z is a $CF_3$ radical, Y is a hydrogen atom, $R^1$ is a methyl group, and $R^2$ is as defined above. Within this group, $R^2$ may be, for example, a carboxyl group either as such or in the form of a salt thereof, or may be an alkoxycarbonyl radical, for example an alkoxycarbonyl radical in which the alkoxy group contains from 1 to 6 carbon atoms.

Another group of compounds according to the invention includes those in which the group Z is a $CF_3$ radical, Y is a chlorine atom, $R^1$ is a methyl group, and $R^2$ is as defined above. Within this group, $R^2$ may be, for example, a carboxyl group either as such or in the form of a salt thereof, or may be an alkoxycarbonyl radical, for example an alkoxycarbonyl radical wherein the alkoxy group contains from 1 to 6 carbon atoms.

A further group of compounds according to the invention includes those in which the group Z is a difluoromethyl or chlorodifluoromethyl radical, Y is hydrogen or chlorine, $R^1$ is a methyl group, and $R^2$ is as defined above. Within this group of compounds, $R^2$ may be, for example, a carboxyl group either as such or in the form of a salt thereof, or may be an alkoxycarbonyl radical, for example an alkoxycarbonyl radical wherein the alkoxy group contains from 1 to 6 carbon atoms.

The compounds of the invention, apart from those in which the group $R^1$ in Formula (I) is a hydrogen atom, contain an asymmetric carbon atom, and are therefore capable of existing in two optically isomeric forms. The present invention includes the dextro- and laevo- rotatory isomers of each compound of the invention, and their mixtures in all proportions.

Particular examples of compounds according to the invention include those listed in Table I below:

TABLE I

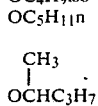

| COMPOUND NO | Z | Y | R¹ | R⁹ | PHYSICAL CONSTANT (MELTING POINT OR BOILING POINT) |
|---|---|---|---|---|---|
| 1 | $CF_3$ | H | $CH_3$ | OH | M.p. 100 |
| 2 | $CF_3$ | H | $CH_3$ | $OCH_3$ | B.p. 134-138/0.05 Torr |
| 3 | $CF_3$ | H | $CH_3$ | $OC_2H_5$ | oil |
| 4 | $CF_3$ | H | $CH_3$ | $OC_3H_7n$ | B.p. 155/0.05 Torr |
| 5 | $CF_3$ | H | $CH_3$ | $OC_4H_9n$ | B.p. 167/0.05 Torr |
| 6 | $CF_3$ | H | $CH_3$ | $OC_4H_9sec$ | B.p. 167/0.05 Torr |
| 7 | $CF_3$ | H | $CH_3$ | $OC_4H_9iso$ | B.p. 165/0.05 Torr |
| 8 | $CF_3$ | H | $CH_3$ | $OC_5H_{11}n$ | oil |
| 9 | $CF_3$ | H | $CH_3$ | $OCH(CH_3)C_3H_7$ | oil |
| 10 | $CF_3$ | H | $CH_3$ | $OCH(CH_3)CH_2CH(CH_3)_2$ | oil |
| 11 | $CF_3$ | H | $CH_3$ | $OCH_2CH(C_2H_5)_2$ | oil |
| 12 | $CF_3$ | H | $CH_3$ | $OC_6H_{13}n$ | oil |
| 13 | $CF_3$ | H | $CH_3$ | Ocyclohexyl | oil |
| 14 | $CF_3$ | H | $CH_3$ | $OCH_2CH(C_2H_5)-C_4H_9$ | oil |
| 15 | $CF_3$ | H | $CH_3$ | $OCH_2Ch_2OCH_3$ | oil |
| 16 | $CF_3$ | H | $CH_3$ | $OC_8H_{17}n$ | oil |
| 17 | $CF_3$ | H | $CH_3$ | $NHC_2H_5$ | m.p. 96-98 |
| 18 | $CF_3$ | H | $CH_3$ | $NH_2$ | m.p. 168-170 |
| 19 | $CF_3$ | H | $CH_3$ | $NHCH_2C_6H_5$ | m.p. 126-128 |
| 20 | $CF_3$ | H | $CH_3$ | $NH.C_6H_4.Clp$ | m.p. 147-149 |
| 21 | $CF_3$ | H | $CH_3$ | $NHCH_2CH_2OH$ | m.p. 72-74 |
| 22 | $CF_3$ | H | $CH_3$ | $NHNH.C_6H_4.Clp$ | solid |
| 23 | $CF_3$ | H | $CH_3$ | $N(CH_3)_2$ | oil |
| 24 | $CF_3$ | H | $CH_3$ | $OCH_2CH=CH_2$ | oil |
| 25 | $CF_3$ | H | $CH_3$ | $OC_6H_5$ | oil |
| 26 | $CF_3$ | H | $CH_3$ | $OC_6H_4.CH_3m$ | oil |
| 27 | $CF_3$ | H | $CH_3$ | $OCH_2C_6H_5$ | oil |
| 28 | $CF_3$ | Cl | $CH_3$ | OH | m.p. 104-107 |
| 29 | $CF_3$ | Cl | $CH_3$ | $OCH_3$ | oil |
| 30 | $CF_3$ | Cl | $CH_3$ | $OC_2H_5$ | oil |
| 31 | $CF_3$ | Cl | $CH_3$ | $OC_3H_7n$ | oil |
| 32 | $CF_3$ | Cl | $CH_3$ | $OC_3H_7iso$ | oil |
| 33 | $CF_3$ | Cl | $CH_3$ | $OC_4H_9n$ | oil |
| 34 | $CF_3$ | Cl | $CH_3$ | $OC_4H_9sec$ | oil |
| 35 | $CF_3$ | Cl | $CH_3$ | $OC_4H_9iso$ | oil |
| 36 | $CF_3$ | Cl | $CH_3$ | $OC_5H_{11}n$ | oil |
| 37 | $CF_3$ | Cl | $CH_3$ | $OCH(CH_3)CH_2CH(CH_3)_2$ | oil |
| 38 | $CF_3$ | Cl | $CH_3$ | Ocyclohexyl | oil |
| 39 | $CF_3$ | Cl | $CH_3$ | $OCH_2CH(C_2H_5)C_4H_9$ | oil |
| 40 | $CF_3$ | Cl | $CH_3$ | $OCH_2CH_2OH$ | oil |
| 41 | $CF_3$ | Cl | $CH_3$ | $OCH_2CH_2OCH_3$ | oil |
| 42 | $CF_3$ | Cl | $CH_3$ | $OC_8H_{17}n$ | oil |
| 43 | $CF_3$ | Cl | $CH_3$ | $N(CH_3)_2$ | oil |
| 44 | $CF_3$ | Cl | $CH_3$ | —N(morpholino)O | m.p. 99-100 |
| 45 | $CF_3$ | Cl | $CH_3$ | $NHC_6H_5$ | m.p. 135-136 |
| 46 | $CF_3$ | Cl | $CH_3$ | $-NHNHC_6H_5$ | m.p. 109-110 |

TABLE I-continued $$\underset{N}{\overset{Z}{\bigvee}}\overset{Y}{\underset{}{\bigvee}}-O-\underset{}{\bigvee}-O\overset{R^1}{\underset{}{CH}}-\overset{}{\underset{\parallel}{C}}R^9$$
$$\phantom{xxxxxxxxxxxxxxxxxxxxxxxxxxxxxxxxxxxx}O$$

| COMPOUND NO | Z | Y | $R^1$ | $R^9$ | PHYSICAL CONSTANT (MELTING POINT OR BOILING POINT) |
|---|---|---|---|---|---|
| 47 | $CF_3$ | Cl | $CH_3$ | $OCH_2{\equiv}CH$ | m.p. 57.5–58.5 |
| 48 | $CF_3$ | Cl | $CH_3$ | $OCH_2CH_2Cl$ | m.p. 79.0–81.5 |
| 49 | $CF_3$ | Cl | $CH_3$ | $O.C_6H_4.Clp$ | m.p. 63–64 |
| 50 | $CF_3$ | Cl | $CH_3$ | $SC_6H_5$ | solid |
| 51 | $CF_3$ | Cl | $CH_3$ | $NHCH_3$ | m.p. 148–149 |
| 52 | $ClCF_2$ | H | $CH_3$ | $OC_2H_5$ | oil |
| 53 | $ClCF_2$ | Cl | $CH_3$ | $OC_2H_5$ | m.p. 61–62 |
| 54 | $ClCF_2$ | Cl | $CH_3$ | $OCH_2Ch_2Cl$ | oil |
| 55 | $ClCF_2$ | Cl | $CH_3$ | $OCH_2CH{=}CH_2$ | oil |
| 56 | $ClCF_2$ | Cl | $CH_3$ | $O.C_6H_4.Clp$ | oil |
| 57 | $ClCF_2$ | Cl | $CH_3$ | $NHCH_3$ | solid |
| 58 | $ClCF_2$ | Cl | $CH_3$ | $NHNH.C_6H_4.Clp$ | solid |
| 59 | $CF_3$ | Br | $CH_3$ | $OC_2H_5$ | oil |
| 60 | $CF_3$ | Br | $CH_3$ | $OC_4H_9n$ | oil |
| 61 | Cl | $CF_3$ | $CH_3$ | $OC_2H_5$ | oil |
| 62 | Cl | $CF_3$ | $CH_3$ | $OC_4H_9n$ | oil |
| 63 | Cl | $CF_3$ | $CH_3$ | $OCH_2CH_2OCH_3$ | oil |
| 64 | Cl | $CF_3$ | $CH_3$ | $-N\bigg(\!\!\!\begin{array}{c}\phantom{x}\\\phantom{x}\end{array}\!\!\!\bigg)O$ | solid |
| 65 | Cl | $CF_3$ | $CH_3$ | $NHC_6H_5$ | solid |
| 66 | Cl | $CF_3$ | $CH_3$ | $OCH_2C_6H_5$ | oil |
| 67 | Cl | $CHF_2$ | $CH_3$ | $OC_2H_5$ | oil |
| 68 | $F_2CH$ | H | $CH_3$ | $OC_2H_5$ | oil |
| 69 | $F_2CH$ | Cl | $CH_3$ | $OC_2H_5$ | oil |
| 70 | $F_2CH$ | Br | $CH_3$ | $OC_2H_5$ | oil |
| 71 | $CF_3$ | $CF_3$ | $CH_3$ | $OC_2H_5$ | oil |
| 72 | $CF_3$ | H | $C_3H_7n$ | $OC_2H_5$ | oil |
| 73 | $CF_3$ | H | $C_2H_5$ | $OC_2H_5$ | oil |
| 74 | $CF_3$ | H | $C_3H_7iso$ | $OC_2H_5$ | oil |
| 75 | $CF_3$ | H | H | $OC_2H_5$ | oil |

The formulae of two further compounds not conveniently listed in Table I are given below:

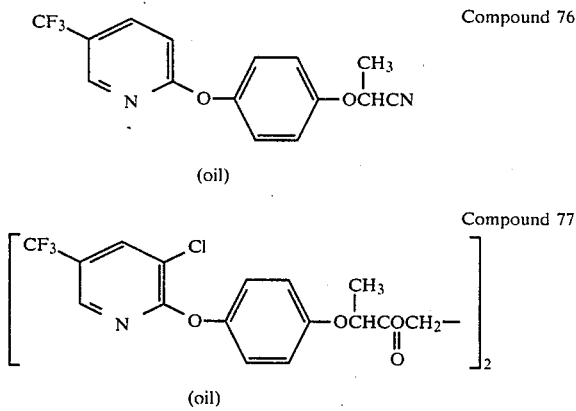

Compound 76
(oil)

Compound 77
(oil)

In the case of a number of the compounds in the above table, a physical constant in the form of a boiling point or melting point is not available since the compounds were often isolated by thin layer chromatography and a high proportion are viscous oils. The structure of the compounds was confirmed by examining their nuclear magnetic resonance spectra, which corresponded with the structure assigned in Table I.

The compounds of the invention are herbicides which are in general substantially more effective against grass species than against broad-leaved species of plants. They may be used to control unwanted grass species growing alone, or at suitable rates of application they may be used to control grass weeds growing among broad-leaved crop plants. The compounds may be either applied to the soil before the emergence of the unwanted grass species (pre-emergence application) or to the above-ground parts of growing grass plants (post-emergence application).

In another aspect, therefore, the invention provides a process of inhibiting the growth of unwanted plants, particularly grass species, which comprises applying to the plants, or to the locus thereof, a herbicidally effective amount of a compound of formula (I) as hereinbefore defined.

The amount of the compound to be applied will depend upon a number of factors, for example the particular plant species whose growth is to be inhibited, but in general an amount of from 0.025 to 5 kilograms per hectare is usually suitable, and preferably from 0.1 to 1.0 kilograms per hectare. The skilled worker in the art will readily be able to determine suitable amounts for use by means of standardised routine tests, without undue experimentation.

The compounds of the invention are preferably applied in the form of compositions, in which the active ingredient is mixed with a carrier comprising a solid or liquid diluent. Preferably the composition further comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, disper-sions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triiso-propyl-naphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol, and octylcresol. Other non-ionic agents are the partial esters derived from long chain fatty acids and hexitol anhydrides, for example sorbitol mono-laurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment. In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

The compounds of the invention may be prepared from appropriately substituted 2-halogenopyridines of formula (II):

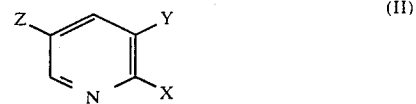

wherein X represents a fluorine, chlorine, bromine, or iodine atom and Y and Z are as defined in formula (I) above. Three general routes are available for converting the halogenopyridines (II) into compounds of the invention; these are described below as Routes A, B and C.

Route A is outlined in the following scheme:

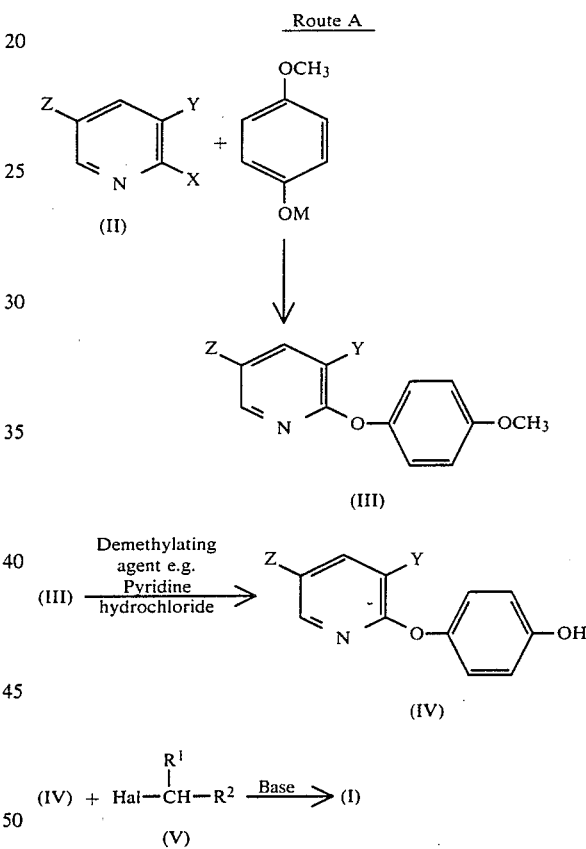

In Route A, the symbols $R^1$, $R^2$, Z and Y have the meanings previously assigned to them, Hal stands for a halogen, preferably chlorine or bromine, and M is a cation, for example sodium.

In Route A, a suitably substituted halogenopyridine (II) is reacted with a metal salt of p-methoxyphenol, for example the sodium salt of p-methoxyphenol. The reaction is preferably carried out in a solvent or diluent, for example methyl ethyl ketone, tetrahydrofuran; dimethylsulphoxide or dimethylacetamide. The 2-p-methoxyphenoxy compound (III) so obtained is then demethylated by a standard procedure, for example by heating with pyridine hydrochloride or with hydrogen bromide in acetic acid, to obtain the corresponding p-hydroxy compound (IV). This in turn is reacted in the form of its metal salt (for example the sodium or potassium salt) with the appropriate halogeno-alkanoic acid derivative (V) to obtain the required compound (I). Preferably this reaction is carried out in a solvent or diluent, for example methyl ethyl ketone.

Route B is outlined in the following scheme:

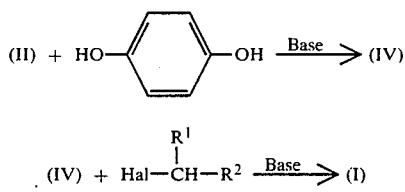

According to Route B, an appropriately substituted 2-halogenopyridine (II) is reacted with hydroquinone in the presence of a base to give the p-hydroxyphenoxy compound (IV) already referred to in Route A. The reaction is preferably carried out in a solvent or diluent for the reactants. Examples of suitable solvents include aprotic solvents, for example dimethylformamide. The reaction is preferably accelerated by heating, for example to a temperature in the range from 50° to 150°. The base used in the reaction may be, for example, an inorganic base, for example sodium or potassium carbonate.

The second stage of Route B is identical with the last stage of Route A and requires no further description.

Route C

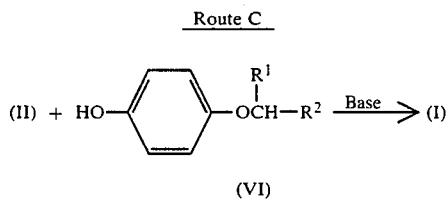

According to Route C, an appropriately substituted 2-halogenopyridine (II) is reacted with a 2-(p-hydroxyphenoxy)propionic acid derivative (VI) in the presence of a base, giving the compound of the invention (I) directly. The derivatives (VI) are known in themselves or may be made by conventional methods. The reaction is preferably carried out in the presence of a solvent or diluent for the reactants. Examples of solvents include lower ketones, for example methyl ethyl ketone. The reaction may be accelerated by heating and may for example be conveniently carried out at the reflux temperature of the solvent. Examples of bases for use in the reaction include inorganic bases, for example anhydrous potassium carbonate. The starting materials (II) used in Routes A, B and C may themselves be prepared by various methods. Compounds containing a fluorinated alkyl group, for example, may be prepared by reacting a corresponding chlorinated compound with a fluorinating agent so as to exchange some or all of the chlorine atoms for fluorine atoms. Thus, 2-chloro-5-trifluoromethyl pyridine is obtainable by reacting 2-chloro-5trichloromethylpyridine with a fluorinating agent, for example antimony trifluoride or liquid hydrogen fluoride. By regulating the amount of fluorinating agent used in the reaction it is possible to obtain compounds with alkyl groups containing both fluorine and chlorine atoms; for example, 2-chloro-5-trichloromethylpyridine may be reacted with a limited amount of antimony trifluoride to obtain 2-chloro-5-chlorodifluoromethylpyridine. In these halogen exchange reactions a proportion of the halogen substituent at the 2-position of the pyridine may also exchange, so that a proportion of the 2-fluorinated compound may be obtained. This is of no practical disadvantage since the halogen at the 2-position is displaced in the subsequent conversion of the halogenopyridine to the compound of the invention. Certain of the chlorinated compounds required as starting materials are believed to be new compounds, for example 2-chloro-5-trichloromethylpyridine and 2,3-dichloro-5-trichloromethylpyridine. These compounds form a further feature of the invention. In addition to their usefulness as intermediates for preparing the compounds of the invention, they have some biological activity as insecticides.

The invention further provides a process of preparing 2-chloro-5-trichloromethyl pyridine which comprises reacting 3-methylpyridine with chlorine in the liquid phase under the influence of ultraviolet light.

The reaction of 3-methylpyridine (as free base or in the form of a salt) with chlorine is generally carried out in an inert organic solvent. Conveniently the solvent is a halogenated hydrocarbon, e.g. carbon tetrachloride; but other solvents may be used, e.g. hydrocarbons or ethers, provided they do not react under the conditions employed to give unacceptable quantities of undesired by-products. Reaction is slow at or below room temperature, and is therefore conveniently speeded up by heat; convenient reaction temperatures are for example in the range 50° to 130° C. The solution may be heated under reflux. It is preferred to use dry reactants and solvents. Ultraviolet light may be supplied to the reaction from a suitable electric lamp, which for greatest efficiency may be immersed in the reaction mixture. The reaction generally gives rise to a mixture of products, from which the desired 2-chloro-5-trichloromethylpyridine may be isolated by conventional methods, e.g. distillation.

In an alternative process for making 2-halogeno-3-or -b 5-triflurormethylpyridines, a 2-halogeno-3- or -5-carboxypyridine may be reacted with sulphur tetrafluoride in the presence of hydrogen fluoride, as shown below for 2-chloro-5-trifluoromethylpyridine:

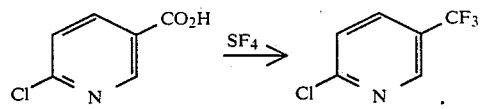

Compounds containing a difluoromethyl group may be prepared by treating the corresponding pyridine aldehyde with sulphur tetrafluoride, as shown below:

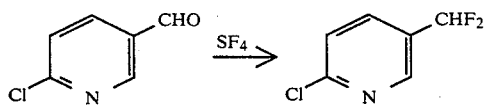

The invention is illustrated by the following Examples, in which all parts are by weight and all temperatures in degrees Centigrade unless otherwise specified.

EXAMPLE 1

This Example illustrates the preparation of a compound according to the invention, namely, ethyl alpha 4(5-trifluoromethyl-2-pyridyloxy)phenoxypropionate (Compound No. 3).

(a) Preparation of 2-chloro-5-trichloromethylpyridine

2-Bromo-5-methylpyridine (55 g) in dry carbon tetrachloride (600 ml) was filtered and then treated with dry hydrogen chloride to give the hydrochloride salt. The solid which separated was broken up and the mixture heated to reflux. Dry chlorine was passed through the boiling mixture for 6½ hours with irradiation by an ultraviolet lamp placed inside the reaction flask. The mixture was then cooled, filtered and evaporated to a pale yellow liquid which solidified on cooling. This was identified as the required chloro compound by its nuclear magnetic resonance spectrum.

(b) Preparation of 2-chloro-5-trifluoromethylpyridine and 2-chloro-5-difluorochloromethylpyridine 2-Chloro-5-trichloromethyl pyridine (18 g) and antimony trifluoride (50 g) were heated together at 140°–145° C. for 1 hour. The mixture was cooled, mixed with ice and concentrated hydrochloric acid, and extracted with ether. The extracts were washed with water, dried with magnesium sulphate, and evaporated. The products from several such preparations were combined and distilled at atmospheric pressure through a short column packed with Fenske rings. The product boiling at 124°–154° C. was collected and identified as 2-chloro-5-trifluoromethylpyridine. Higher boiling fractions were redistilled at a pressure of 20 mm mercury to give 2-chloro-5-difluorochloromethylpyridine, boiling at 82° to 90° C.

(c) Preparation of 2-p-methoxyphenoxy-5-trifluoromethyl pyridine

Sodium hydride (4.2 g of 50% dispersion in oil, washed with petroleum) was stirred in dry dimethylsulphoxide (100 ml) and a solution of p-methoxy phenol (10.4 g) in dimethylsulphoxide (100 ml) added over a period of a few minutes. The mixture was stirred for 30 minutes to form the sodium salt. To the solution was added 2-chloro-5trifluoromethylpyridine (15.0 g) in dimethyl sulphoxide (80 ml) over a period of a few minutes. The mixture was then heated to 70°–75° for 3 hours and left to cool overnight. Thin-layer chromatography showed that only one compound was present. The mixture was diluted to 1.5 liters with water, and then extracted with ether (3×600 ml). The ether extracts were washed several times with water and then with molar sodium hydroxide solution, and finally with water (2×200 ml). The ether extract was dried and evaporated to give the required pyridine compound as a brown oil.

(d) Preparation of 2-hydroxyphenoxy-5-trifluoromethyl pyridine 2-p-Methoxyphenoxy-5-trifluoromethylpyridine (10.5 g) in glacial acetic acid (100 ml) and 48% hydrobromic acid (50 ml) were stirred and heated under reflux for 7½ hours. The solution was then evaporated and the remaining oil treated with sodium bicarbonate solution and shaken with ether (2×300 ml). The ether extract was shaken with 2-molar sodium hydroxide solution (200 ml) and then water (150 ml). The aqueous layers were combined, acidified with 2-molar hydrochloric acid and extracted with ether (2×300 ml). The ether extract was dried and evaporated to give a brown oil identified as 2-p-hydroxyphenoxy-5-trifluoromethylpyridine.

(e) Preparation of compound no. 3 of Table I 2-p-Hydroxyphenoxy-5-trifluoromethylpyridine (0.22 g), ethyl alpha-bromopropionate (0.24 g) and potassium carbonate (0.18 g) in methyl ethyl ketone (5 ml) were stirred, and heated under reflux for 2 hours. The mixture was left to cool overnight, then filtered, and the residue washed with methyl ethyl ketone. The filtrate and washings were evaporated and the remaining oil subjected to a high vacuum to remove traces of solvent. The nuclear magnetic resonance spectrum of the oil was consistent with the structure assigned and the compound was identified as compound no. 3.

(f) Preparation of compound no. 8

The product from (e) (0.3 g) was dissolved in n-pentanol (15 ml) containing concentrated sulphuric acid (2 drops). The mixture was heated to reflux for 3½ hours. The solvent was removed and the residue taken up in ether and washed with saturated sodium bicarbonate solution. The ether solution was dried and evaporated to a colourless oil which was purified by preparative scale thin layer chromatography on silica gel with an 80:20 mixture of petroleum (b.p. 60°–80° C.) and ether as the solvent. The nuclear magnetic resonance spectrum of the product identified it as the required pentyl ester.

(g) Preparation of compound no. 1

The product from (e) (0.14 g) in isopropanol (2 ml) was stirred at room temperature for 1¾ hours with an aqueous solution of sodium hydroxide (1.6 ml of a solution containing 1 g NaOH per 100 ml water). The mixture was evaporated in a vacuum and the residue taken up in water, acidified, and extracted with ether (2×50 ml). The ether extracts yielded an oil identified as the required carboxylic acid.

(h) Preparation of compounds 2, 4 to 7, and 14

Following the procedure described in paragraph (e) above, but using in each case the appropriate alpha bromopropionic ester instead of ethyl alpha bromopropionate, compounds no. 2, 4 to 7 inclusive, and no. 14 were prepared.

(i) Preparation of 2[4(5-trifluoromethylpyridyl-2-oxy)phenoxy]propionyl chloride The carboxylic acid prepared as described in paragraph (g) above (1.2 g) was heated under reflux with thionyl chloride (20 ml) for 1 hour and the excess of thionyl chloride then removed under reduced pressure. The residue was mixed with toluene and the toluene evaporated under reduced pressure to remove traces of thionyl chloride. The propionyl chloride derivative was obtained as an oil.

(j) Preparation of compound no. 17 to 23

The acid chloride as prepared in (i) above (0.78 g) was added to an excess of aqueous ethylamine (20 ml; solution containing 70 g ethylamine per 100 ml). The excess of ethylamine solution was removed under reduced pressure. The residue was diluted with water and extracted with ether. The ether solution was washed with 2-molar hydrochloric acid and water, and dried and evaporated. The residue was recrystallised from petroleum (b.p. 60°–80°) to give the ethylamide (Compound no. 17) with a melting point of 96°–98°.

Following this procedure, compounds 18 to 23 were prepared, using the appropriate amine instead of ethylamine in each case.

(k) Preparation of compounds 9 to 13, 15, 16, 24 and 27

The acid chloride as prepared in (i) above (0.87 g) was dissolved in allyl alcohol and heated at 100° for 1 hour. The excess of alcohol was removed under reduced pressure and the remaining oil washed with water and 2-molar hydrochloric acid and dissolved in ether. The ether solution was dried and evaporated and the remaining oil purified by thin-layer chromatography on silica gel using a mixture of equal volumes of ether and petroleum (b.p. 60°–80°) as eluent. The allyl ester (compound no. 24) was obtained as a colourless oil. Compounds 9 to 13, 15, 16 and 27 were prepared by a similar procedure, using in each case the appropriate alcohol in place of allyl alcohol.

(l) Preparation of compounds 25 and 26

The acid chloride as prepared in (i) above (0.94 g) in dry ether containing pyridine (2 ml) was mixed with phenol (1 molar proportion) and the solution left overnight. The solution was evaporated and the residue purified by thin layer chromatography to give compound 25 as a clear oil. Compound 26 was similarly prepared.

EXAMPLE 2

This illustrates the preparation of 2-chloro-5-trichloromethylpyridine by chlorination of 3-methylpyridine under the influence of ultra-violet light.

3-Methylpyridine (10 ml) was dissolved in dry carbon tetrachloride (300 ml). The solution was heated to reflux (about 80°) and dry chlorine gas passed through the boiling mixture for 3 hours while it was at the same time irradiated internally from a 100 watt ultra-violet lamp producing light of wavelength 185 nm. Preparative thin layer chromatography (silica, chloroform/cyclohexane) on an evaporated sample of the solution thus obtained gave three main products in total overall yield of 10–15%; the most abundant of these was identified by its nuclear magnetic resonance spectrum as the desired 2-chloro-5-trichloromethylpyridine. This was confirmed by mass spectrograph analysis of the solution obtained. The other two major products were 2-chloro-3-trichloromethyl pyridine and a di(trichloromethyl)pyridine, present in amount of about half, and about one-tenth, respectively, of the major product.

EXAMPLE 3

This Example illustrates the preparation of 2-chloro-5-trichloromethylpyridine from a salt of 3-methylpyridine.

3-Methylpyridine (15 g) in dry carbon tetrachloride (200 ml) was treated with dry HCl gas to give the hydrochloride. The oily mixture thus obtained was stirred and heated to reflux. Dry chlorine gas was bubbled into the refluxing mixture for 4 hours while illuminating it internally from the ultraviolet lamp used in Example 1. The reaction mixture was then cooled, and separated by decantation into solution and oily solid. The latter was purified, and shown to contain unreacted 3-methylpyridine salt. The former was evaporated to an oily semi-solid, which was shown by thin-layer chromatography to have the characteristics of 2-chloro-5-trichloromethylpyridine.

EXAMPLE 4

This Example describes the preparation of 2-chloro-5-trifluoromethylpyridine by a method alternative to that of Example 1.

6-Chloronicotinic acid (23.6 g), sulphur tetrafluoride (37.4 g) and anhydrous hydrogen fluoride (18.7 g) were heated in an autoclave with stirring for 8 hours at 120°. The mixture was cooled, poured on to ice, and neutralised with concentrated sodium hydroxide at 0°. The mixture was extracted with ether and the extracts washed with water, dried, and evaporated. The residue was distilled and the fraction boiling at 140°–150° collected. Analysis indicated that this consisted of 2-chloro-5-trifluoromethylpyridine with some 2-fluoro-5-trifluoromethylpyridine.

EXAMPLE 5

This Example describes the preparation of 2-chloro-5-trifluoromethylpyridine by a method alternative to that of Examples 1 and 4.

2-Chloro-5-trichloromethylpyridine (30.8 g) and anhydrous hydrogen fluoride (80 g) were heated for 10 hours at 200° stirring in an autoclave. The mixture was cooled, poured on to ice, and neutralised at 0°. The mixture was filtered and the residue and filtrate extracted with ether. The ether extracts were washed with water, dried, and evaporated to give an oil. This was distilled and the fraction boiling at 140°–154° collected. Analysis indicated that this consisted of 2-chloro-5-trifluoromethylpyridine with some 2-fluoro-5-trifluoromethylpyridine.

EXAMPLE 6

This Example illustrates the preparation of compound no. 30 of Table I by Route A.

(a) Preparation of 2-amino-3-bromo-5-methylpyridine

2-Amino-5-methylpyridine (108 g) in glacial acetic acid (300 ml) was heated to 90°–100° C. while bromine (160 g) in acetic acid (55 ml) was slowly added with stirring. When addition was complete, the mixture was stirred and heated for a further 30 minutes and then allowed to cool overnight. The solid which separated was filtered off and mixed with ice and the mixture neutralised with concentrated ammonia, keeping the temperature at 0° to 5° C. The solid was collected, washed with water, and dried to give the bromo-compound.

(b) Preparation of 3-bromo-2-chloro-5-methylpyridine

The product from (a) (145 g) was dissolved in concentrated hydrochloric acid (750 ml) and water (450 ml) and the solution cooled to −10° C. Sodium nitrite (54 g) in cold water (450 ml) was added dropwise with stirring over a period of 90 minutes while the mixture was kept at −5° C. The solution was stirred for a further 2 hours, and then basified with concentrated ammonia, keeping the temperature below 20° C. The solid which separated was washed with water, dried, dissolved in ether (1500 ml) and washed with cold sodium hydroxide solution (1M; 1 liter). The ether solution was washed twice with water (1 liter portions), dried, and evaporated to give the required 3-bromo-2-chloro-5-methylpyridine.

Preparation of 2,3-dichloro-5-trichloromethylpyridine

The product from (b) (64 g) in dry carbon tetrachloride (650 ml) was treated with dry hydrogen chloride. The precipitate was broken up and the suspension heated under reflux while dry chlorine was bubbled into the mixture, with illumination from an ultra-violet light source. After 4½ hours, the mixture was cooled, filtered, and the filtrate evaporated to give the required 2,3-dichloro-5-trichloromethylpyridine. The mass spectrum was consistent with the structure assigned to this compound.

(d) Preparation of 2,3-dichloro-5-trifluoromethylpyridine

The product from (c) (1.0 g) and antimony trifluoride (3.0 g) were heated together at 170°–180° for 30 minutes. The mixture was then cooled, mixed with ice and water, and extracted with ether. The ether extracts gave a brown oil containing a mixture of 2,3-dichloro-5-trifluoromethylpyridine and 3-chloro-2-fluoro-5-trifluoromethylpyridine with a minor amount of 2,3-dichloro-3-chlorodifluoromethylpyridine.

(e) Preparation of 3-chloro-2-p-methoxyphenoxy-5-trifluoromethylpyridine p-Methoxyphenol (1.5 g) was added to a suspension of sodium hydride (0.6 g 50% oil dispersion, washed with petroleum) in dry dimethyl sulphoxide (30 ml) and the mixture stirred for 15 minutes. A solution of the combined products (1.5 g) from several preparations carried out as described in paragraph (d), in dimethylsulphoxide (20 ml) was added to the reaction mixture and heated to 60° C. for four hours. A further amount of sodium hydride (0.3 g of 50% oil dispersion, washed with petroleum), and potassium carbonate (1.38 g) was added. Heating was continued for another 4 hours. The mixture was poured into ice and water, and extracted with ether (400 ml). The ether extracts were washed with water, dilute sodium hydroxide, and water, dried, and evaporated to give the product.

(f) Preparation of 3-chloro-2-hydroxyphenoxy-5-trifluoromethylpyridine

The product from (e) (2 g) was heated with pyridine hydrochloride (20 g) at 170°–180° C. for 6 hours. The mixture was cooled, diluted with dilute hydrochloric acid, and extracted with ether. The ether extracts gave an oily solid which was purified by preparative thin layer chromatography using silica as the adsorbent and 6% ethanol-chloroform as the solvent.

(g) Preparation of compound no. 30 of Table I

The product from (f) (0.16 g), ethyl alpha bromopropionate (0.3 g), and potassium carbonate (0.25 g) were heated and stirred under reflux in methyl ethyl ketone (10 ml) for 2 hours. The mixture was cooled and filtered. Evaporation of the filtrate gave an oil which was heated in a vacuum to remove traces of solvent. The oil was identified as compound no. 30 by examination of its mass spectrum and its purity was confirmed by gas-liquid chromatography.

2,3-Dichloro-5-trichloromethylpyridine was also prepared by an alternative route, as follows:

(h) Preparation of 2-amino-3-chloro-5-methylpyridine

2-Amino-5-methylpyridine (10.8 g) in concentrated hydrochloric acid (100 ml) was kept at 10°–15° C. while hydrogen peroxide (30%, 21 ml) was added dropwise with stirring. When addition was complete the mixture was stirred for 1¾ hours without cooling, and poured on to ice (about 200 g). The mixture was brought to pH 8–9 by adding concentrated ammonia dropwise, keeping the temperature at 0° C. by adding ice. The solution was extracted with chloroform (2×300 ml). The chloroform extracts yielded the required chloro-compound as a yellow solid.

(i) Preparation of 2-bromo-3-chloro-5-methylpyridine

The product from paragraph (h) (5.7 g) in hydrobromic acid (48%; 50 ml) was cooled to −15° C. to −10° C. and bromine (2.6 ml) was added dropwise with stirring. The temperature was then kept at −5° C. to 0° C. while sodium nitrite (5.53 g) in water (12 ml) was added dropwise over a period of 45 minutes. When addition was complete, the mixture was stirred a further 30 minutes at 0° C. and poured on to ice. The mixture was made slightly alkaline by dropwise addition of concentrated ammonia, keeping the temperature at 0° C. with added ice. The mixture was extracted with ether (150 ml). The ether extract was washed with water, sodium bisulphite solution, and water, and then dried and evaporated. The residue was taken up in petroleum (b.p. 40°–60° C.) and the solution filtered and evaporated. The residue was identified as 2-bromo-3-chloro-5-methylpyridine.

(j) Preparation of 2,3-dichloro-5-trichloromethylpyridine

The product from paragraph (i) (2.9 g) in dry carbon tetrachloride (250 ml) was treated with dry hydrogen chloride to convert it to the hydrochloride. Chlorine was passed through the suspension which was kept at 80° C. and illuminated by an ultra-violet lamp inside the reaction flask. After three hours the solvent was removed, leaving a residue of 2,3-dichloro-5-trichloromethylpyridine.

EXAMPLE 7

This Example illustrates the preparation of 2,3-dichloro-5-trifluoromethylpyridine by fluorination of 2,3-dichloro-5-trichloromethylpyridine, using a fluorinating agent alternative to that of Example 6.

2,3-Dichloro-5-trichloromethylpyridine (35 g) was heated with anhydrous hydrogen fluoride (100 g) in an autoclave at 200° for 10 hours with stirring. The cooled reaction mixture was poured on to ice and neutralised with sodium hydroxide at 0°. The mixture was extracted with methylene chloride (750 ml). The extracts were washed with water (500 ml), sodium carbonate solution (500 ml) and water (500 ml), dried, and evaporated. The remaining oil was distilled and the fraction of boiling point 77°–83°/25 Torr was collected and identified as the required pyridine derivative.

EXAMPLE 8

This Example further illustrates the preparation of 2,3-dichloro-5-trifluoromethylpyridine.

Antimony trifluoride (61 g) was melted under a vacuum to remove moisture. The cooled material was broken up and heated to 65°–70° while antimony pentachloride (6.6 g) was added dropwise with stirring. 2,3-

Dichloro-5-trichloromethylpyridine (40 g) was then added dropwise to the mixture and the whole heated to 160° over 45 minutes. The mixture was cooled and steam distilled. The oil which distilled over was extracted with ether (2×100 ml). The ether extract was washed with tartaric acid solution then water, sodium bicarbonate, and water, and dried. The remaining oil was distilled. The fraction boiling at 71°–80°/18 Torr was identified as the required pyridine derivative.

EXAMPLE 9

This Example illustrates the preparation of 3-chloro-5-trifluoromethyl-2-p-hydroxyphenoxypyridine by Route B.

Dry dimethylformamide (30 ml) was de-aerated by heating under reflux under a stream of argon for 30 minutes. Hydroquinone (4.95 g) and anhydrous potassium carbonate (6.84 g) were added and heated for 90 minutes under reflux. 2,3-Dichloro-5-trifluoromethylpyridine (6.48 g) in dry, de-aerated dimethyl formamide (30 ml) was added to the above mixture over a period of 4 hours. The mixture was allowed to cool overnight and diluted with water (500 ml). The mixture was acidified with dilute hydrochloric acid and extracted with ether (2×400 ml). The ether extract was washed with water (2×500 ml) and extracted with dilute sodium hydroxide solution (300 ml). The ether extract was washed with water and the aqueous fractions combined and re-acidified with hydrochloric acid. The acidified aqueous solution was extracted with chloroform (2×400 ml). The chloroform extract yielded a light brown oil which on trituration with petroleum (b.p. 30°–40° ) gave a colourless solid identified as the required 3-chloro-5-trifluoromethyl-2-p-hydroxyphenoxypyridine.

EXAMPLE 10

This Example illustrates the preparation of ethyl 2[4(3-chloro-5-trifluoromethylpyridyl-2-oxy) phenoxy]propionate (compound no 30 Table I).

The product from Example 9 (1.0 g) was stirred and heated under reflux in methyl ethyl ketone (25 ml) with potassium carbonate (0.5 g) and ethyl 2-bromopropionate (1.0 g) for 4 hours. The mixture was cooled and filtered and the filtrate evaporated to give an oil which was purified by thin-layer chromatography on two 2 millimeter thick plates, each 20 by 20 centimeters in size, using a mixture of 20 volumes of ether and 100 volumes of hexane as the eluent. The product was extracted with ethanol. Evaporation of the ethanol gave a colourless oil identified as compound no 30 by its nuclear magnetic resonance spectrum.

EXAMPLE 11

Following the procedure described in Example 10, compounds no 29, 31 to 39, 41 and 42 of Table I were prepared, using the appropriate ester of 2-bromopropionic acid in each case.

EXAMPLE 12

This Example illustrates the preparation of 2[4(3-chloro-5-trifluoromethylpyridyl-2-oxy)phenoxy]propionic acid (compound no 28 of Table I).

Compound no 31 of Table I (2.19 g) in isopropanol (20 ml) was treated at room temperature dropwise with a solution of sodium hydroxide (0.23 g) in water (20 ml). The mixture was stirred at room temperature for 4 hours, then diluted to 300 ml with water. The solution was extracted with methylene dichloride (2×50 ml) and acidified with 2-molar hydrochloric acid. The acidified solution was extracted with methylene dichloride (2×150 ml) and the extract dried and evaporated to give an oil. This solidified on standing and was dried at 85° in a vacuum to give compound no 28 with a melting point of 104°–107°.

EXAMPLE 13

This Example illustrates the preparation of compounds 43 to 45 and 48 to 51 of Table I.

(a) Preparation of 2[4(3-chloro-5-trifluoromethylpyridyl-2-oxy)phenoxy]-propionyl chloride.

The carboxylic acid prepared by the method of Example 12 (16.5 g) was dissolved in an excess of thionyl chloride (200 ml) and heated under reflux for 2 hours. The excess of thionyl chloride was removed under reduced pressure to give the acid chloride as a yellow oil. This was taken up in dry ether (220 ml) and the solution used to prepare compounds 40, 43 to 45, 48 to 51 and 77 as follows. Since the procedures are conventional, only brief details are given, and these are tabulated below.

| COMPOUND NO | AMOUNT OF ACID CHLORIDE SOLUTION USED | REACTANT AND PROCEDURE | PURIFICATION OF PRODUCT |
| --- | --- | --- | --- |
| 43 | 40 ml | 20 ml of aqueous dimethylamine at room temperature | *TLC using silica gel/ether |
| 44 | 20 ml | 0.75 g of morpholine in ether (20 ml) at room temperature overnight | Recrystallisation from petroleum (b.p. 60–80°) and toluene |
| 45 | 20 ml | 0.85 g aniline in ether (20 ml) at room temperature overnight | Recrystallisation from petroleum (b.p. 60–80°) and n-propanol |
| 48 | 20 ml | 6 ml 2-chloroethanol 2 hr at 100° | TLC |
| 49 | 20 ml | 0.55 g p-chlorophenol, 1 ml pyridine, in 20 ml ether at room temperature overnight | TLC using silica gel/ mixture of ether with petroleum (b.p. 60–80°) in ratio of 1 volume to 5 |
| 50 | 20 ml | 0.45 g thiophenol, 1 ml pyridine, 20 ml ether at room | TLC as for compound 49 |

| COMPOUND NO | AMOUNT OF ACID CHLORIDE SOLUTION USED | REACTANT AND PROCEDURE | PURIFICATION OF PRODUCT |
| --- | --- | --- | --- |
| | | -continued | |
| 51 | 1.5 g of acid converted to acid chloride as above | temperature overnight 20 ml of 20% aqueous methylamine at room temperature | Recrystallisation from petroleum (b.p. 60–80°) and toluene |
| 40 and 77 | 0.8 g of acid converted to acid chloride as above | 20 ml of ethylene glycol at room temperature for 3 hours | TLC using silica gel/ ether |

*TLC stands for thin layer chromatography

EXAMPLE 14

This Example illustrates the preparation of compound 46 of Table I.

The solution prepared in paragraph (a) of Example 13 (20 ml) was added to a solution of phenyl hydrazine (0.95 g) in dry ether (20 ml) at room temperature and the mixture stirred overnight. The mixture was then diluted with water and acidified with 2-molar hydrochloric acid. The ether layer was separated, washed with water, and dried. Evaporation of the ether gave the phenylhydrazide as a solid of melting point 109°–110°.

EXAMPLE 15

This Example illustrates the preparation of compound no 47 of Table I.

The solution prepared in paragraph (a) of Example 13 (20 ml) was added to a solution of propargyl alcohol (0.25 g) in ether (20 ml) containing potassium carbonate (0.75 g). The mixture was stirred at room temperature overnight. Chromatography indicated that no reaction had taken place. The mixture was filtered and the filtrate evaporated to an oil. Propargyl alcohol (5 ml) was added and the mixture heated for 2 hours at 100°. The mixture was cooled and the excess of propargyl alcohol removed under reduced pressure. The residue was purified by thin layer chromatography, using silica gel as the solid phase and a mixture of ether (1 volume) and petroleum (b.p. 80°–80°; 5 volumes) as the eluent. The product isolated in this way was a colourless oil which solidified on storage to give compound no 47 with a melting-point of 57.5°–58.5°.

EXAMPLE 16

This Example illustrates the preparation of ethyl alpha 4(5-difluorochloro-2-pyridyloxy)phenoxy propionate. (Compound no 52) by Route A.

(a) Preparation of 5-difluorochloromethyl-2-p-methoxyphenoxy pyridine

The 2-chloro-5-difluorochloromethylpyridine prepared in Example 1 (b) (1.0 g) in dimethylsulphoxide (10 ml) was added to a solution of p-methoxyphenol (0.62 g) previously reacted with sodium hydride (0.24 g of 50% oil dispersion, washed with petroleum) in dimethyl sulphoxide (15 ml). The mixture was stirred and heated to 60°–65° C. for 5 hours, poured into ice, and extracted with ether. The ether extracts were washed with water, dilute sodium hydroxide, and water, dried, and evaporated to give an oil identified as the required p-methoxy compound.

(b) Preparation of 5-difluorochloromethyl-2-p-hydroxyphenoxypyridine

The product from (a) (1.0 g) was dissolved in glacial acetic acid (12 ml) and aqueous hydrobromic acid (48%; 5 ml) added. The reaction mixture was stirred and heated under reflux for 3½ hours. The mixture was cooled and evaporated under reduced pressure. The residue was taken into ether and washed with sodium bicarbonate solution and water. The ether solution was dried and evaporated to yield an oil which partially solidified. This was purified by preparative thin layer chromatography on silica gel using a mixture of 6% ethanol in chloroform as the solvent.

(c) Preparation of compound no 52

The product from (b) (0.18 g) was heated under reflux for 2½ hours in methyl ethyl ketone (10 ml) with ethyl alpha bromopropionate (0.3 g) and potassium carbonate (0.25 g). The mixture was cooled and the solids filtered off and washed with methyl ethyl ketone. The filtrate and washings were evaporated in a vacuum to give an oil. The nuclear magnetic resonance spectrum of this oil was consistent with its structure assignment as compound no 52.

EXAMPLE 17

This Example illustrates the preparation of ethyl 2[4(3-chloro-5-chlorodifluoromethylpyridyl-2-oxy)-phenoxy]propionate (compound no 53 of Table I) using Route C 2,3-Dichloro-5-chlorodifluoromethylpyridne (1.0 g) and ethyl 2-(4-hydroxyphenoxy)propionate (1.0 g) in methyl ethyl ketone (10 ml) containing potassium carbonate (1.0 g) were stirred and heated under reflux for 3 hours. The mixture was cooled and filtered. The residue was washed with methylethyl ketone and the filtrate and washings evaporated under reduced pressure to give an oil. The oil was purified by thin-layer chromatography using silica gel as the solid phase and a mixture of ether (1 volume) and petroleum (b.p. 60°–80°, 4 volumes) as the eluent. The product was a colourless oil which solidified on storage to give compound no 53 with a melting point of 61°–62°.

EXAMPLE 18

This Example illustrates the preparation of compounds 54 to 58 of Table I.

(a) Preparation of propyl 2[4(3-chloro-5-chlorodifluoromethylpyridyl-2-oxy)-phenoxy]propionate 2,3-Dichloro-5-chlorodifluoropyridine was reacted with propyl 2(4-hydroxyphenoxy)propionate in methyl ethyl ketone as described for the corresponding ethyl ester in Example 17. The propyl ester so obtained was purified by dissolving it in a mixture of ether (1 vol) and petroleum (b.p. 60°-80°, 4 volumes) and passing it through a column of silica gel.

(b) Preparation of carboxylic acid from (a)

The propyl ester was dissolved in isopropanol and treated slowly with sodium hydroxide solution as described in Example 12. The carboxylic acid was isolated as described in Example 12.

(c) Preparation of acid chloride from (b)

The 2[4(3-chloro-5-chlorodifluoromethylpyridyl-2-oxy)phenoxy]propionic acid, prepared in (b) was heated at 100° C. for 2 hours with excess of thionyl chloride and the excess of thionyl chloride then removed under reduced pressure. The acid chloride was then used to prepare compounds 54 to 58 as follows. Since the procedures are conventional, only brief details are given, and these are tabulated below.

| COMPOUND NO | REACTION PROCEDURE | PURIFICATION OF PRODUCT |
| --- | --- | --- |
| 54 | Reflux with excess of 2-chloroethanol for 2 hours | TLC using silica gel/ether |
| 55 | Reflux with excess of allyl alcohol for 2 hours | TLC using silica gel/ether |
| 56 | Reaction with p-chlorophenol in ether in presence of pyridine at room temperature overnight | Product substantially pure |
| 57 | Reaction with excess of aqueous methylamine solution | TLC using silica gel/ether |
| 58 | Reaction with excess of p-chlorophenyl-hydrazine | TLC using silica gel/ether |

EXAMPLE 19

This Example describes the preparation of 3-bromo-2-chloro-5-trifluoromethylpyridine.

(a) Preparation of 3-bromo-2-chloro-5-pyridine carboxylic acid

3-Bromo-2-chloro-5-methylpyridine (30 g) in water (650 ml) containing potassium permanganate (60 g) was stirred and heated under reflux for 3 hours. Further potassium permanganate (20 g) was then added and the mixture heated and stirred for another 2½ hours. The mixture was steam-distilled to remove unchanged starting material, and then filtered while hot. The residue was washed with hot water. The filtrate and washings were cooled and acidified with concentrated hydrocholoric acid. The solid which separated was extracted with ether. The ether extract was dried and evaporated to give 3-bromo-2-chloropyridine-5-carboxylic acid.

(b) Preparation of 3-bromo-2-chloro-5-trifluoromethyl pyridine

The product from (a) (12 g), sulphur tetrafluoride (20 g) and anhydrous hydrogen fluoride (10 g) were stirred and heated to 120° for 8 hours in an autoclave. The product was poured on to ice and neutralised with concentrated sodium hydroxide at 0°. The mixture was extracted with ether (3×100 ml) and the extracts washed with water, sodium bicarbonate solution, and water. The extracts were dried and evaporated to give a brown oil. This was distilled and the fraction boiling at 88°-93° collected. This was identified as 3-bromo-2-fluoro-5-trifluoromethylpyridine.

The product of paragraph (b) was used as starting material for the preparation of compounds 59 and 60 of Table I, following Route C.

EXAMPLE 20

This Example describes the preparation of 2,5-dichloro-3-trifluoromethylpyridine and 2,5-dichloro-3-difluoromethylpyridine.

(a) Preparation of 2,5-dichloro-3-trichloromethylpyridine and 2,5-dichloro-3-dichloromethylpyridine 2,5-Dichloro-3-methylpyridine (37 g) in dry carbon tetrachloride (500 ml) was treated with sufficient dry hydrogen chloride to precipitate the pyridine as its hydrochloride. The mixture was then stirred and heated under reflux while dry chlorine was passed through and the solution irradiated by an internal ultra-violet lamp. Chlorination was continued for 3½ hours and the solution then evaporated to give an oily solid. This was washed with petroleum (b.p. 30°-40°). The residue was identified as consisting mainly of 2,5-dichloro-3-trichloromethyl pyridine. The filtrate was evaporated to give an oil identified as consisting mainly of 2,5-dichloro-3-dichloromethylpyridine.

(b) Preparation of 2,5-dichloro-3-trifluoromethyl pyridine 2,5-Dichloro-3-trichloromethylpyridine from (a) above (30 g) in anhydrous hydrogen fluoride (90 g) was stirred and heated to 200° in an autoclave for 10 hours. The contents were cooled, poured into ice, and neutralised with concentrated sodium hydroxide at 0°. The aqueous layer was decanted from the oily organic layer and the latter extracted with portions of methylene chloride (total 750 ml). The methylene chloride extracts were dried and evaporated to give an oil. This was distilled and the fraction boiling at 70°-76° at 20 Torr collected. Analysis indicated that this comprised 2,5-dichloro-3-trifluoromethylpyridine containing about 10 percent by weight of 5-chloro-2-fluoro-3-trifluoromethylpyridine.

(c) Preparation of 2,5-dichloro-3-difluoromethylpyridine 2,5-Dichloro-3-dichloromethylpyridine (20 g) in anhydrous hydrogen fluoride (60 g) was stirred and heated in an autoclave for 10 hours at 200°. The mixture was then cooled, poured on to ice and neutralised with concentrated sodium hydroxide solution at 0°. The aqueous layer was decanted from the organic layer and the organic layer dissolved in methylene dichloride. The methylene dichloride solution was used to extract the aqueous layer. The methylene dichloride extract was washed with water, sodium carbonate solution, and water, and then dried and evaporated. The remaining oil was distilled. The fraction boiling at 85° to 98° at 22 Torr was collected and redistilled in a micro spinning band apparatus. The fraction boiling at 87°-87.5°/25 Torr was identified as 95% pure 2,5-dichloro-3-difluoromethylpyridine.

The 2,5-dichloro-3-trifluoromethylpyridine obtained as described above was converted by Route C into compounds 61 and 62 of Table I, and the 2,5-dichloro-3-difluoromethylpyridine was converted by Route C into compound 67.

Compounds 63 to 66 were prepared by reaction of 2[4(5-chloro-3-trifluoromethylpyridyl-2-oxy)phenoxy]propionyl chloride with, respectively, 2-methyoxyethanol, morpholine, aniline, and benzyl alcohol, following the procedures described in paragraphs (j) and (k) of Example 1. The propionyl chloride required for these preparations was made by reaction of the corresponding acid with thionyl chloride following the procedure described in paragraph (i) of Example 1. The required carboxylic acid was obtained by hydrolysis of its propyl ester with sodium hydroxide following the procedure described in paragraph (g) of Example 1.

EXAMPLE 21

This Example illustrates the preparation of ethyl 2[4(5-difluoromethylpyridyl-2-oxy)phenoxy]propionate (compound no 68 of Table I.

(a) Preparation of 2-chloro-5-formyl pyridine

2-Chloro-5-cyanopyridine (15 g) in 90% formic acid (60 ml) and water (15 ml) was stirred at 55° and treated with Raney nickel/aluminum alloy (15 g). The mixture was stirred at 55° for 9½ hours and the warm solution filtered. The residue was washed with warm ethanol (ca. 25 ml) and the filtrates combined and diluted to 600 ml with water. The solution was extracted with ether (3×250 ml). The ether extract was washed with aqueous sodium carbonate and water, dried, and evaporated to give a pale yellow solid identified as 2-chloro-5-formylpyridine.

(b) Preparation of 2-chloro-5-difluoromethylpyridine

The product from (a) (9.9 g) and sulphur tetrafluoride (15.5 g) were heated in an autoclave at 153°–155° for 6 hours. The autoclave was then cooled and vented. The mixture was basified with aqueous sodium carbonate and extracted with methylene dichloride. The methylene dichloride was dried and evaporated, and the remaining oil distilled. The fraction boiling at 156°–164° was collected and identified as 2-chloro-5-difluoromethylpyridine containing some 2-fluoro-5-difluoromethylpyridine.

(c) Preparation of compound no 68

The product from (b) (0.44 g) and ethyl 2-(4-hydroxyphenoxy)propionate (0.63 g) in methyl ethyl ketone (10 ml) containing potassium carbonate (0.5 g) were stirred and heated under reflux for 13½ hours. The mixture was cooled and filtered, and the filtrate evaporated. The remaining oil was purified by thin layer chromatography using silica gel as the solid phase and a mixture of chloroform (75 parts by volume), petroleum (b.p. 60°–80°, 25 parts) and ethyl acetate (5 parts) as the liquid phase. The product obtained in this way was an oil.

EXAMPLE 22

This Example illustrates the preparation of ethyl 2[4(3-bromo-5-difluoromethylpyridyl-2-oxy)phenoxy]propionate (compound no 70 of Table I).

(a) Preparation of 3-bromo-2-chloro-5-formylpyridine

3-Bromo-2-chloro-5-cyanopyridine (8.6 g) in 90% formic acid (40 ml) and water (10 ml) were treated with Raney nickel/aluminium alloy (8.0 g) and the mixture stirred and heated to 55°–60° for 6 hours. The mixture was left to stand for two days, and then filtered. The filtrate was diluted to 500 ml with water and extracted with ether (2×250 ml). The ether extract was washed with aqueous sodium carbonate, dried, and evaporated to give an oil. The oil was diluted with toluene which was then removed under reduced pressure. The residue was diluted with a little ether, the solution filtered, and the filtrate evaporated to give an oil identified as the required aldehyde.

(b) Preparation of 3bromo-2-chloro-5-difluoromethyl pyridine

The product from (a) (5.6 g) and sulphur tetrafluoride (9 g) were heated in an autoclave for 6 hours at 150°. The autoclave was cooled and vented and the contents treated with aqueous sodium carbonate. The solution was extracted with methylene dichloride. The methylene dichloride extract was dried and evaporated to give an oil which was distilled under reduced pressure. The fraction boiling at 85°–95°/15 Torr was collected and identified as 3-bromo-2-chloro-5-difluoromethylpyridine containing a small proportion of 2-chloro-3-fluoro-5-difluoromethylpyridine or its 2-fluoro-3-chloro isomer.

(c) Preparation of compound no 70

The product from (b) (0.5 g), ethyl 2-(4-hydroxyphenoxy)propionate (0.465 g), and potassium carbonate (0.5 g) in methyl ethyl ketone (10 ml) were stirred and heated under reflux for 5½ hours. The mixture was filtered and evaporated to give a yellow oil. This was purified by thin layer chromatography using silica gel as the solid phase and as the liquid phase the mixture described in paragraph (c) of Example. The major band was extracted with ethanol. Evaporation of the ethanol yielded an oil which gas-liquid chromatography showed to contain 96% of the main component. This was identified as compound 70 by its nuclear magnetic resonance spectrum.

EXAMPLE 23

This Example illustrates the preparation of ethyl 2[4(3-chloro-5-difluoromethylpyridyl-2-oxy)phenoxy]propionate (compound no 69 of Table I) by Route C.

(a) Preparation of 2,3-dichloro-5-difluoromethyl

A mixture of 2,3-dichloro-5-formylpyridine (3 g) pyridine containing a minor proportion of 2,3,5-trichloropyridine, was heated with sulphur tetrafluoride (4.5 g) in an autoclave for 6 hours. The cooled reaction mixture was treated with aqueous sodium carbonate and extracted with methylene dichloride. The extract was dried and evaporated and the residue distilled in a micro spinning band apparatus. The fraction boiling at 65°–100° was collected. Gas-liquid chromatography indicated that this was a mixture of about 60% of 3-chloro-2-fluoropyridine and 40% of the required 2,3-dichloro-5-difluoromethylpyridine.

(b) Preparation of compound 69

The product from (a) (0.65 g), ethyl 2-(4-hydroxyphenoxy)propionate (1.0 g) were heated under reflux in methyl ethyl ketone (10 ml) with stirring for 4½ hours. The solution was filtered, and the filtrate evaporated to give an oil. The oil was purified by thin-layer chromatography, using silica gel as the solid phase and a mixture of chloroform (75 parts by volume), a petroleum (b.p. 60°–80°, 25 parts) and ethyl acetate (5 parts) as the eluent. The product eluted was a mixture. This was chromatographed again using a mixture of ether (1 part by volume) and petroleum (b.p. 60°–80°; 2 parts) as the eluent. Two bands developed; the faster moving band was extracted with ethanol and the ethanol extracts evaporated. The remaining oil was identified as compound no 69 by its nuclear magnetic resonance spectrum.

EXAMPLE 24

This Example describes the preparation of 2-chloro-3,5-bistrifluoromethylpyridine.

(a) Preparation of 3,5-bis-trifluoromethylpyridine 3,5-Pyridine-dicarboxylic acid (17.5 g) containing a proportion of pyridine 2,5-dicarboxylic acid was heated with sulphur tetrafluoride (72 g) and hydrogen fluoride (40 g) in an autoclave for 8 hours at 150°–151°. The cooled reaction mixture was neutralised at 0° with concentrated potassium hydroxide solution. The mixture was extracted with methylene dichloride, and the extract dried and evaporated. The residue was distilled and the fraction boiling at 119°–128° collected. The NMR spectrum indicated a mixture of 3,5- and 2,5-bis-trifluoromethylpyridines.

(b) Preparation of 2-chloro-3,5-bis-trifluoromethyl pyridine

The foregoing product (3.0 g) in dry carbon tetrachloride (250 ml) was stirred and heated under reflux while chlorine (dried) was passed slowly through the solution and the solution was irradiated by a UV lamp. After 6½ hours the carbon tetrachloride was distilled off and the residue distilled in a spinning band apparatus. The fraction boiling at 75°–85° was collected and identified as 2-chloro-3,5-bis-trifluoromethylpyridine containing a proportion of 2,5- and 3,5-bistrifluoromethylpyridine.

The 2-chloro-bis-trifluoromethylpyridine so obtained was converted into compound 71 of Table I by following Route C.

EXAMPLE 25

This Example illustrates the preparation of compound no 76. 2-(p-Hydroxyphenoxy)-5-trifluoromethylpyridine (1.0 g) was heated under reflux with 2-chloropropionitrile (1 molar equivalent) and potassium carbonate (1g) for three days. The mixture was filtered and the solvent removed under reduced pressure to give an oil, which was purified by thin-layer chromatography on silica gel using a mixture of equal volumes of ether and petroleum (b.p. 60°–80°).

EXAMPLE 26

This Examples illustrates the preparation of compound no 73.

2(p-Hydroxyphenoxy)-5-trifluoromethylpyridine (1.25 g), potassium carbonate (0.75 g), ethyl alpha bromobutyrate (0.96 g) and methyl ethyl ketone (25 ml) were heated under reflux for 6 hours. The cooled solution was filtered and the solution evaporated to give an oil. This was purified by passage through a column of silica gel using a mixture of 20% by volume of ether and hexane as the eluent. Compound no 73 was obtained as a colourless oil.

Following this procedure, but using the appropriate alpha bromo alkanoic ester in place of ethyl alpha-bromobutyrate, compounds 72, 74 and 75 were prepared. The starting esters were ethyl alpha bromovalerate, ethyl alpha bromo isovalerate, and ethyl bromoacetate respectively.

EXAMPLE 27

This Example illustrates the herbicidal properties of the compounds of the invention. Each compound was formulated for test by mixing it with 5 ml of an emulsion prepared by diluting 100 ml of a solution containing 21.8 grams per liter of Span 80 and 78.2 grams per liter of Tween 20 in methyl cyclohexanone to 500 ml with water. Span 80 is a Trade Mark for a surface-active agent comprising sorbitan monolaurate. Tween 20 is a Trade Mark for a surface-active agent comprising a condensate of twenty molar proportions of ethylene oxide with sorbitan mono-oleate. The mixture of the compound and the emulsion was shaken with glass beads and diluted to 12 ml with water.

The spray composition so prepared was sprayed on to young pot plants (post-emergence test) of the species named in Table II below, at a rate equivalent to 1000 liters per hectare. Damage to plants was assessed 14 days after spraying by comparison with untreated plants, on a scale of 0 to 3 where 0 is no effect and 3 represents 75 to 100% kill. In a test for pre-emergence herbicidal activity, seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the same scale of 0 to 3. A dash (-) in the table of results means that no test was made. The results are given in Table II below:

TABLE II

| COMPOUND NO | RATE OF APPLICATION kg/ha | PRE- (A) OR POST- (B) EMERGENCE APPLICATION | TEST PLANTS ||||||
|---|---|---|---|---|---|---|---|---|
| | | | Lt | To | Ot/Av | Ll | Cn | St |
| 1 | 0.4 | A | 0 | 0 | 2 | 3 | 0 | 3 |
| | | B | 0 | 0 | 0 | 0 | 0 | 0 |
| 5 | 0.5 | A | 0 | 0 | 3 | 3 | 0 | 3 |
| | | B | 0 | 0 | 3 | 3 | 0 | 3 |
| 8 | 0.4 | A | — | 0 | 3 | 3 | 0 | 3 |
| | | B | — | 0 | 3 | 3 | 0 | 3 |
| 17 | 0.8 | A | 2 | 0 | 3 | 3 | 0 | 3 |
| | | B | 0 | 0 | 3 | 3 | 0 | 3 |
| 18 | 0.8 | A | 0 | 0 | 3 | 3 | 0 | 3 |
| | | B | 0 | 0 | 3 | 3 | 0 | 3 |
| 19 | 0.8 | A | 0 | 0 | 3 | 3 | 0 | 3 |
| | | B | 0 | 0 | 3 | 3 | 0 | 3 |
| 20 | 0.8 | A | 0 | 0 | 3 | 3 | 0 | 3 |
| | | B | 0 | 0 | 3 | 3 | 0 | 3 |
| 21 | 0.8 | A | 0 | 0 | 3 | 3 | 0 | 3 |
| | | B | 0 | 0 | 3 | 3 | 0 | 3 |
| 22 | 0.8 | A | 0 | 0 | 3 | 3 | 0 | 3 |
| | | B | 0 | 0 | 3 | 3 | 0 | 3 |
| 23 | 0.8 | A | 0 | 0 | 3 | 3 | 0 | 3 |
| | | B | 0 | 0 | 1 | 3 | 0 | 3 |
| 24 | 0.08 | A | 0 | 0 | 3 | 3 | 0 | 3 |
| | | B | 0 | 0 | 1 | 3 | 0 | 3 |
| 25 | 0.08 | A | 0 | 0 | 2 | 3 | 0 | 3 |
| | | B | 0 | 0 | 3 | 3 | 0 | 3 |
| 26 | 0.08 | A | 0 | 0 | 1 | 3 | 0 | 3 |
| | | B | 0 | 0 | 3 | 3 | 0 | 3 |
| 27 | 0.08 | A | 0 | 0 | 0 | 3 | 0 | 3 |
| | | B | 0 | 0 | 3 | 2 | 0 | 3 |
| 29 | 0.08 | A | 0 | 0 | 3 | 3 | 0 | 3 |

TABLE II-continued

| COMPOUND NO | RATE OF APPLICATION kg/ha | PRE- (A) OR POST- (B) EMERGENCE APPLICATION | TEST PLANTS | | | | | |
|---|---|---|---|---|---|---|---|---|
| | | | Lt | To | Ot/Av | Ll | Cn | St |
| 31 | 0.25 | B | 0 | 0 | 3 | 3 | 0 | — |
| | | A | 0 | 0 | 3 | 3 | 0 | 3 |
| | | B | 0 | 0 | 3 | 3 | 0 | 3 |
| 41 | 0.08 | A | 0 | 0 | 3 | 3 | 0 | 3 |
| | | B | 2 | 0 | 3 | 3 | 1 | — |
| 43 | 0.8 | A | 0 | 0 | 3 | 3 | 0 | 3 |
| | | B | 0 | 0 | 3 | 3 | 0 | 3 |
| 44 | 0.8 | A | 0 | 0 | 3 | 3 | 0 | 3 |
| | | B | 0 | 0 | 3 | 3 | 0 | 3 |
| 45 | 0.8 | A | 0 | 0 | 3 | 3 | 0 | 3 |
| | | B | 0 | 0 | 3 | 3 | 0 | 3 |
| 46 | 0.8 | A | 0 | 0 | 3 | 3 | 0 | 3 |
| | | B | 0 | 0 | 3 | 3 | 0 | 3 |
| 47 | 0.08 | A | 3 | 0 | 3 | 3 | 0 | 3 |
| | | B | 0 | 0 | 3 | 3 | 0 | 3 |
| 48 | 0.08 | A | 0 | 0 | 3 | 3 | 0 | 3 |
| | | B | 0 | 0 | 3 | 3 | 0 | 3 |
| 49 | 0.08 | A | 0 | 0 | 3 | 3 | 0 | 3 |
| | | B | 0 | 0 | 3 | 2 | 0 | 3 |
| 50 | 0.08 | A | 0 | 0 | 3 | 3 | 0 | 3 |
| | | B | 0 | 0 | 3 | 0 | 0 | 3 |
| 51 | 0.8 | A | 2 | 0 | 3 | 3 | 0 | 3 |
| | | B | 0 | 0 | 3 | 3 | 0 | 3 |
| 52 | 0.4 | A | — | 0 | 1 | 0 | 0 | 2 |
| | | B | — | 0 | 3 | 2 | 0 | 3 |
| 53 | 0.08 | A | 0 | 0 | 3 | 3 | 0 | 3 |
| | | B | 0 | 0 | 1 | 0 | 0 | 3 |
| 59 | 0.08 | A | 1 | 0 | 2 | 3 | — | 3 |
| | | B | 0 | 0 | 2 | 3 | 0 | — |
| 60 | 0.08 | A | 0 | 0 | 3 | 3 | 0 | 3 |
| | | B | 3 | 0 | 3 | 3 | 0 | — |
| 61 | 0.08 | A | 0 | 0 | 0 | 3 | 0 | 2 |
| | | B | 0 | 0 | 3 | 2 | 0 | — |
| 62 | 0.08 | A | 0 | 0 | 0 | 3 | 0 | 0 |
| | | B | 0 | 0 | 0 | 1 | 0 | — |
| 73 | 10.0 | A | 3 | 0 | 3 | 3 | 0 | 3 |
| | | B | 1 | 0 | 3 | 3 | 0 | 3 |
| 74 | 10.0 | A | 0 | 0 | 0 | 3 | 0 | 3 |
| | | B | 0 | 0 | 3 | 3 | 0 | 3 |
| 75 | 10.0 | A | 2 | 0 | 3 | 3 | 0 | 3 |
| | | B | 3 | 3 | 3 | 3 | 0 | 3 |
| 76 | 0.5 | A | 0 | 0 | 3 | 3 | 0 | 3 |
| | | B | 0 | 0 | 3 | 3 | 0 | 2 |
| 77 | 0.08 | A | 0 | 0 | 3 | 3 | 0 | 3 |
| | | B | 0 | 0 | 0 | 0 | 0 | — |

The names of the test plants are as follows:
Lt: Lettuce
To: Tomato
Ot/Av: Cultivated oats and wild oats (*Avena fatua*). Wild oats are used in the post-emergence test and cultivated oats in the pre-emergence test.
Ll: *Lolium perenne* (perennial rye grass)
Cn: *Cyperus rotundus*
St: *Setaria viridis*

The results in Table II clearly illustrate the selectivity of the compounds of the invention, the grass species used in the test being severely damaged or killed while the dicotyledonous plants were essentially unharmed.

EXAMPLE 28

This Example illustrates the herbicidal properties of the compounds of Table I. Tests were carried out as described in Example 27. The compound was formulated by mixing an appropriate amount of the compound with 5 ml of an emulsion prepared by diluting 160 ml of a solution containing 21.8 grams per liter of Span 80 and 78.2 grams per liter of Tween 20 in methylcyclohexanone to 500 ml with water. The mixture of the compound and emulsion was shaken with glass beads and diluted to 40 ml with water. Damage to plants was assessed on a scale of 0 to 5 where 0 is 0 to 20% damage and 5 is complete kill. In the table of results, a dash (-) means that no test was made. The results are given in Table III below:

TABLE III

| COMPOUND NO | RATE OF APPLICATION kg/ha | PRE- (A) OR POST- (B) EMERGENCE APPLICATION | TEST PLANTS | | | | | | | | | | | | | |
|---|---|---|---|---|---|---|---|---|---|---|---|---|---|---|---|---|
| | | | Sb | Rp | Ct | Sy | Mz | Ww | Rc | Sn | Ip | Am | Pi | Ca | Po | Xs |
| 1 | 0.4 | A | 1 | 0 | 0 | 0 | 5 | 5 | 5 | — | 0 | 0 | 0 | 0 | 0 | 0 |
| | | B | 2 | 1 | 0 | 0 | 5 | 3 | 3 | 0 | 0 | 0 | 0 | 0 | 0 | 0 |
| 5 | 0.5 | A | 0 | 0 | 1 | 0 | 5 | 5 | 5 | 1 | 1 | 1 | 0 | 0 | 0 | 3 |
| | | B | 0 | 0 | 0 | 0 | 5 | 4 | 3 | 0 | 0 | 0 | 0 | 0 | 0 | 0 |
| 8 | 0.4 | A | 0 | 0 | 0 | 1 | 5 | 5 | 5 | — | 0 | 0 | 0 | 3 | 0 | 0 |
| | | B | 2 | 2 | 1 | 0 | 5 | 4 | 4 | 0 | 0 | 0 | 0 | 0 | 1 | 0 |
| 30 | 0.4 | A | 0 | 0 | 1 | 0 | 5 | 5 | 5 | — | 0 | 2 | 1 | 0 | 1 | 0 |
| | | B | 1 | 0 | 1 | 0 | 5 | 5 | 5 | 1 | 0 | 0 | 0 | 0 | 0 | 0 |
| 31 | 0.08 | A | 2 | 0 | 0 | 0 | 4 | 4 | 5 | 0 | 2 | 0 | 0 | 0 | 0 | 0 |
| | | B | 2 | 0 | 0 | 0 | 5 | 3 | 3 | 2 | 1 | 0 | 0 | 0 | 0 | — |
| 52 | 1.0 | A | 0 | 0 | 0 | 0 | 4 | 5 | 5 | — | 0 | 1 | 0 | 0 | 1 | 0 |
| | | B | 0 | 1 | 2 | 0 | 5 | 4 | 4 | 1 | 0 | 0 | 0 | 0 | 2 | 0 |
| 53 | 1.5 | A | 3 | 0 | 0 | 1 | 4 | 5 | 5 | 0 | 0 | 3 | 0 | 1 | 0 | 0 |
| | | B | 1 | 0 | 1 | 0 | 5 | 4 | 4 | 1 | 0 | 3 | 0 | 1 | 2 | 0 |
| 59 | 0.5 | A | 2 | 1 | 0 | 0 | 4 | 4 | 5 | 2 | 0 | 1 | 0 | 0 | 0 | — |
| | | B | 0 | 1 | 0 | 0 | 5 | 3 | 3 | 0 | 0 | 0 | 0 | 0 | 0 | 0 |
| 60 | 0.5 | A | 2 | 0 | 0 | 0 | 4 | 4 | 5 | 2 | 0 | 0 | 0 | 2 | 0 | — |
| | | B | 0 | 0 | 0 | 0 | 5 | 3 | 3 | 0 | 0 | 0 | 0 | 1 | 0 | 0 |
| 61 | 1.0 | A | 0 | 0 | 0 | 0 | 4 | 2 | 2 | 2 | 0 | 0 | 0 | 0 | 1 | — |
| | | B | 1 | 1 | 1 | 0 | 5 | 3 | 2 | 0 | 0 | 0 | 0 | 0 | 1 | 1 |
| 62 | 1.0 | A | 0 | 0 | 0 | 0 | 3 | 4 | 5 | 0 | 0 | 0 | 0 | 2 | 0 | — |
| | | B | 0 | 2 | 0 | 0 | 5 | 3 | 2 | 0 | 0 | 0 | 0 | 0 | 1 | 0 |
| 67 | 1.0 | A | 1 | 0 | 0 | 0 | 4 | 5 | 5 | 2 | 2 | 0 | 0 | 0 | — | 0 |
| | | B | 0 | 0 | 0 | 0 | 5 | 4 | 3 | 1 | 0 | 1 | 0 | 0 | 0 | — |
| 72 | 1.5 | A | 2 | 0 | 0 | 0 | 2 | 0 | 1 | 0 | 0 | 1 | 0 | 1 | 0 | 0 |
| | | B | 0 | 0 | 0 | 0 | 1 | 0 | 0 | 0 | 2 | 0 | 0 | 0 | 0 | 0 |

PRE- (A) OR

TABLE III-continued

| COMPOUND NO | RATE OF APPLICATION kg/ha | POST- (B) EMERGENCE APPLICATION | TEST PLANTS | | | | | | | | | |
|---|---|---|---|---|---|---|---|---|---|---|---|---|
| | | | Ab | Cv | Ot/Av | Dg | Pu | St | Ec | Sh | Ag | Cn |
| 1 | 0.4 | A | 0 | — | 4 | — | 4 | 4 | 5 | 5 | 5 | 0 |
| | | B | 0 | 0 | 4 | 3 | 0 | 3 | 5 | 5 | 3 | 0 |
| 5 | 0.5 | A | 1 | — | 4 | 5 | 0 | 4 | 5 | 3 | 3 | 1 |
| | | B | 0 | 0 | 4 | 3 | 0 | 4 | 5 | 5 | 3 | 0 |
| 8 | 0.4 | A | 0 | — | 4 | — | 3 | 4 | 5 | 4 | 5 | 0 |
| | | B | 0 | — | 4 | 4 | 1 | 4 | 5 | 5 | 4 | 0 |
| 30 | 0.4 | A | 2 | — | 5 | — | 4 | 5 | 5 | 5 | 5 | 0 |
| | | B | 1 | — | 5 | 5 | 3 | 5 | 5 | 5 | 5 | 0 |
| 31 | 0.08 | A | 1 | — | 4 | 5 | 4 | 4 | 4 | 3 | 0 | 0 |
| | | B | 0 | 0 | 3 | — | 2 | 5 | 5 | 5 | 4 | 0 |
| 52 | 1.0 | A | 0 | — | 3 | — | 1 | 4 | 5 | 4 | 5 | 0 |
| | | B | 0 | — | 4 | 4 | 0 | 4 | 5 | 5 | 2 | 0 |
| 53 | 1.5 | A | 0 | — | 4 | 5 | 5 | 5 | 5 | 4 | 2 | 0 |
| | | B | 0 | 0 | 5 | 5 | 4 | 5 | 5 | 5 | 4 | 0 |
| 59 | 0.5 | A | 0 | — | 4 | 5 | 5 | 5 | 5 | 5 | 2 | 0 |
| | | B | 0 | 0 | 5 | 4 | 3 | 5 | 5 | 5 | 4 | 0 |
| 60 | 0.5 | A | 0 | — | 4 | 5 | 4 | 5 | 5 | 5 | 4 | 0 |
| | | B | 0 | 0 | 4 | 4 | 3 | 5 | 5 | 5 | 4 | 0 |
| 61 | 1.0 | A | 0 | — | 4 | 5 | 1 | 5 | 5 | — | 4 | 0 |
| | | B | 1 | 0 | 3 | 4 | 2 | 4 | 5 | 5 | 3 | 0 |
| 62 | 1.0 | A | 0 | — | 4 | 5 | 2 | 5 | 5 | 4 | 2 | 0 |
| | | B | 0 | 0 | 4 | 4 | 2 | 5 | 5 | 4 | 2 | 0. |
| 67 | 1.0 | A | 0 | — | 5 | 5 | 4 | 5 | 5 | 4 | 1 | 2 |
| | | B | 0 | 0 | 3 | — | 3 | 5 | 5 | 5 | 4 | 0 |
| 72 | 1.5 | A | 1 | — | 0 | 1 | 0 | 0 | 2 | 0 | 0 | 0 |
| | | B | 0 | 0 | 0 | 0 | 0 | 0 | 0 | 1 | 1 | 0 |

The names of the test plants were as follows:
Sb: Sugar beet
Rp: Rape
Ct: Cotton
Sy: Soya bean
Mz: Maize
Ww: Winter wheat
Rc: Rice
Sn: *Senecio vulgaris*
Ip: *Ipomoea purpurea*
Am: *Amaranthus retroflexus*
Pi: *Polygonum aviculare*
Ca: *Chenopodium album*
Po: *Portulaca oleracea*
Xs: *Xanthium spinosum*
Ab: *Abutilon theophrastii*
Cv: *Convolvulus arvensis*
Ot/Av: Cultivated oats and wild oats (*Avena fatua*) Wild oats are used in the post-emergence test and cultivated oats in the pre-emergence test
Dg: *Digitaria sanguinalis*
Pu: *Poa annua*
St: *Setaria viridis*
Ec: *Echinochloa crus-galli*
Sh: *Sorghum halepense*
Ag: *Agropyron repens*
Cn: *Cyperus rotundus*

EXAMPLE 29

This Example further illustrates the selective herbicidal activity of the compounds of the invention. Tests were carried out on a range of crop plants and weeds, in which compounds were applied to the crops at ten times the rate at which they were applied to the weeds. The test procedure was similar to that described in Example 27. Damage was assessed 20 days after spraying, on a scale of 0 to 10 where 0 is no effect and 10 is complete kill. Each result given in the table below is the mean figure for damage to three plants. The selective nature of the herbicidal compounds of the invention will be readily apparent from the table of results, since even though the compounds were applied to the crops at ten times the rate which caused severe damage to the grass species in the test, there was little or no damage to the crop plants.

| COMPOUND NO | RATE OF APPLICATION (kg/ha) TO CROPS AND WEEDS | CROPS | | | WEEDS | | | |
|---|---|---|---|---|---|---|---|---|
| | | Sy | Ct | Sb | Ec | Dg | Av | Al |
| 2 | 0.25 + 0.025 | 0 | 0 | 0 | 3 | 2 | 2 | 3 |
| 3 | 0.5 + 0.05 | 0 | 0 | 0 | 4 | 3 | 1 | 1 |
| 4 | 0.75 + 0.075 | 3 | — | 0 | 9 | 9 | 6 | 6 |
| 5 | 1.0 + 0.1 | 3 | 1 | 1 | 9 | 9 | 6 | 8 |
| 6 | 0.25 + 0.025 | 0 | 0 | 0 | 6 | 5 | 2 | 0 |
| 7 | 0.5 + 0.05 | 0 | 0 | 0 | 6 | 9 | 1 | 6 |
| 8 | 0.75 + 0.075 | 1 | 2 | 0 | 9 | 9 | 5 | 9 |
| 9 | 0.71 + 0.1 | 0 | 0 | 0 | 9 | 9 | 3 | 8 |
| 10 | 0.25 + 0.025 | 0 | 0 | 0 | 1 | 0 | 0 | 0 |
| 11 | 0.5 + 0.05 | 0 | 0 | 0 | 7 | 8 | 1 | 4 |
| 12 | 0.75 + 0.075 | 0 | 2 | 1 | 9 | 9 | 6 | 9 |
| 13 | 1.0 + 0.1 | 0 | 0 | 0 | 9 | 9 | 6 | 9 |
| 14 | 0.25 + 0.025 | 0 | 0 | 0 | 5 | 7 | 2 | 3 |
| 15 | 0.5 + 0.05 | 0 | 0 | 2 | 9 | 9 | 4 | 6 |
| 16 | 1.0 + 0.1 | 0 | 0 | 0 | 9 | 9 | 5 | 9 |
| 28 | 0.125 + 0.0125 | 0 | 0 | 0 | 2 | 1 | 1 | 1 |
| 29 | 0.25 + 0.025 | 0 | 0 | 0 | 9 | 9 | 8 | 2 |
| 30 | 0.5 + 0.05 | 0 | 1 | 0 | 9 | 9 | 9 | 8 |
| 31 | 1.0 + 0.1 | 1 | 3 | 0 | 9 | 9 | 9 | 8 |
| 32 | 0.125 + 0.0125 | 0 | 0 | 0 | 2 | 4 | 4 | 0 |
| 33 | 0.25 + 0.025 | 0 | 0 | 0 | 9 | 9 | 8 | 4 |
| 34 | 0.5 + 0.05 | 0 | 1 | 0 | 9 | 9 | 9 | 9 |
| 35 | 0.75 + 0.075 | 0 | 2 | 1 | 9 | 9 | 9 | 8 |
| 36 | 0.125 + 0.0125 | 0 | 1 | 0 | 6 | 8 | 5 | 2 |
| 37 | 0.25 + 0.025 | 0 | 0 | 0 | 2 | 3 | 6 | 0 |
| 38 | 0.5 + 0.05 | 0 | 1 | 0 | 9 | 9 | 9 | 8 |
| 39 | 0.75 + 0.075 | 0 | 0 | 0 | 9 | 9 | 9 | 5 |
| 40 | 0.125 + 0.0125 | 0 | 0 | 0 | 4 | 4 | 5 | 0 |
| 41 | 0.25 + 0.025 | 0 | 0 | 0 | 9 | 9 | 8 | 5 |
| 42 | 0.5 + 0.05 | 0 | 0 | 0 | 9 | 9 | 9 | 7 |

The meanings of the abbreviations for the names of the test plants have been given in Example 28 except for Al, which stands for *Alopecurus myosuroides*.

EXAMPLE 30

This Example illustrates the herbicidal activity of compounds of the invention against a perennial grass species, in comparison with a previously known herbicidal compound of a similar type. The previously known compound was compound A below:

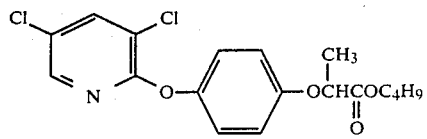

Compounds no 5 and 31 of Table I were compared with compound A. In the test, pieces of the rhizome of *Sorghum halepense* 5 to 8 centimeters long and containing 2 to 3 nodes were buried in compost in plastic trays in the greenhouse. The compounds were formulated for test as described in Example 28. In a pre-emergence test the compounds were sprayed on to the compost three days after the rhizome segments had been buried. The surface was then covered with more compost and watered. In a post-emergence test, the rhizone segments were left for 20 days, when shoots with two to four true leaves had emerged, and sprayed. Assessments of herbicidal damage were made three weeks after treatment.

In the test, three replicates were used for each treatment. The results are expressed as percentage damage to the plants, and are the mean of two separate tests. The figures for percentage damage are given in the tables below:

| PRE-EMERGENCE RESULTS | | | | |
|---|---|---|---|---|
| COMPOUND | RATE OF APPLICATION, kg/ha | | | |
| NO | 0.125 | 0.25 | 0.5 | 1.0 |
| A | 11 | 55 | 69 | 100 |
| 5 | 58 | 98 | 100 | 98 |
| 31 | 85 | 88 | 100 | 100 |

| POST-EMERGENCE RESULTS | | | | |
|---|---|---|---|---|
| COMPOUND | RATE OF APPLICATION, kg/ha | | | |
| NO | 0.125 | 0.25 | 0.5 | 1.0 |
| A | 58 | 85 | 94 | 100 |
| 5 | 66 | 88 | 100 | 100 |
| 31 | 96 | 100 | 100 | 100 |

It can be seen from the above tables that the compounds of the invention are more herbicidally effective than Compound A at lower rates.

EXAMPLE 31

This Example illustrates the herbicidal properties of further compounds of the invention. The compounds were tested by the procedure set forth in Example 27 and the results expressed in the same way; the results are given in the following table, which may be regarded as a continuation of Table II.

| COMPOUND NO | RATE OF APPLICATION kg/ha | PRE- (A) OR POST- (B) EMERGENCE APPLICATION | TEST PLANTS | | | | | |
|---|---|---|---|---|---|---|---|---|
| | | | Lt | To | Ot/Av | Ll | Cn | St |
| 54 | 1.0 | A | 0 | 0 | 3 | 3 | 0 | 3 |
| | | B | 2 | 1 | 3 | 3 | 0 | 3 |
| 55 | 1.0 | A | 0 | 0 | 3 | 3 | 0 | 3 |
| | | B | 2 | 1 | 3 | 3 | 0 | 3 |
| 56 | 1.0 | A | 0 | 0 | 3 | 3 | 0 | 3 |
| | | B | 1 | 0 | 3 | 3 | 0 | 3 |
| 57 | 1.0 | A | 0 | 0 | 3 | 3 | 0 | 3 |
| | | B | 1 | 0 | 3 | 3 | 0 | 3 |
| 58 | 1.0 | A | 0 | 0 | 3 | 3 | 0 | 3 |
| | | B | 0 | 0 | 3 | 3 | 0 | 3 |
| 63 | 5.0 | A | 0 | 0 | 3 | 3 | 0 | 3 |
| | | B | 1 | 0 | 3 | 3 | 0 | 3 |
| 64 | 1.0 | A | 0 | 0 | 0 | 3 | 0 | 3 |
| | | B | 0 | 0 | 0 | 0 | 0 | 3 |
| 65 | 1.0 | A | 0 | 0 | 1 | 3 | 0 | 3 |
| | | B | 0 | 0 | 0 | 0 | 0 | 3 |
| 66 | 1.0 | A | 0 | 0 | 3 | 3 | 0 | 3 |
| | | B | 0 | 0 | 2 | 3 | 0 | 3 |
| 68 | 1.0 | A | 0 | 0 | 0 | 3 | 0 | 3 |
| | | B | 0 | 0 | 1 | 2 | 0 | 3 |
| 69 | 1.0 | A | 0 | 0 | 3 | 3 | 0 | 3 |
| | | B | 0 | 0 | 3 | 3 | 0 | 3 |
| 70 | 1.0 | A | 0 | 0 | 3 | 3 | 0 | 3 |
| | | B | 0 | 0 | 3 | 3 | 0 | 3 |
| 71 | 1.0 | A | 0 | 0 | 3 | 3 | 0 | 3 |
| | | B | 0 | 0 | 3 | 3 | 0 | 3 |

I claim:
1. 2,3-dichloro-5-trichloromethylpyridine.

* * * * *